US009931218B2

(12) United States Patent
May et al.

(10) Patent No.: US 9,931,218 B2
(45) Date of Patent: Apr. 3, 2018

(54) METHOD OF IMPLANTING A KNEE PROSTHESIS BASED ON BONE DENSITY

(71) Applicant: Biomet Manufacturing, LLC, Warsaw, IN (US)

(72) Inventors: Brian M. May, Warsaw, IN (US); Duke A. Fox, Warsaw, IN (US); Joshua B. Catanzarite, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 614 days.

(21) Appl. No.: 13/663,769

(22) Filed: Oct. 30, 2012

(65) Prior Publication Data

US 2014/0121715 A1   May 1, 2014

(51) Int. Cl.
*A61F 2/38* (2006.01)
*A61B 17/58* (2006.01)
*A61F 2/46* (2006.01)
*A61F 2/30* (2006.01)

(52) U.S. Cl.
CPC ............ *A61F 2/389* (2013.01); *A61F 2/4657* (2013.01); *A61F 2/30942* (2013.01); *A61F 2002/30607* (2013.01); *A61F 2002/4662* (2013.01); *A61F 2002/4666* (2013.01)

(58) Field of Classification Search
None
See application file for complete search history.

(56) References Cited

U.S. PATENT DOCUMENTS

| 881,047 A | 3/1908 | Ballantine |
|---|---|---|
| 1,763,639 A | 6/1930 | Roudie |
| 2,421,449 A | 6/1947 | Zuber |
| 3,038,330 A | 6/1962 | Criche |
| 3,498,120 A | 3/1970 | MacMillan |
| 4,182,163 A | 1/1980 | Hoffmeyer |
| 4,336,710 A | 6/1982 | Miller |
| 4,776,202 A | 10/1988 | Brar et al. |
| 4,887,459 A | 12/1989 | Thomas |
| 5,176,026 A | 1/1993 | Leeb et al. |
| 5,471,868 A | 12/1995 | Nolan |
| 6,536,263 B1 | 3/2003 | Wood et al. |
| 6,976,387 B2 | 12/2005 | Anthe et al. |
| 7,878,987 B2 | 2/2011 | Hansma et al. |
| 7,900,499 B2 | 3/2011 | Zhang |
| 7,966,866 B2 | 6/2011 | Hansma et al. |
| 8,163,027 B2 | 4/2012 | Rhodes et al. |
| 9,155,500 B2 * | 10/2015 | Bowen ................ A61B 5/4504 |

(Continued)

*Primary Examiner* — Tatiana Nobrega
*Assistant Examiner* — Jessica Weiss
(74) *Attorney, Agent, or Firm* — Schwegman Lundberg & Woessner, P.A.

(57) ABSTRACT

A method of implanting a prosthesis based on bone density of a bone is provided. A first bone density of the bone may be determined at a first portion of the bone. A second bone density of the bone may be determined at a second portion of the bone. A first desired amount of bone removal may be determined at the first portion of the bone based on the first bone density. A second desired amount of bone removal may be determined at the second portion of the bone based on the second bone density. The desired amounts of bone may be removed from the first and second portions of the bone. A prosthesis may be selected and implanted.

19 Claims, 3 Drawing Sheets

(56) References Cited

U.S. PATENT DOCUMENTS

| | | | |
|---|---|---|---|
| 2005/0203632 A1* | 9/2005 | Daniels | A61F 2/389 623/20.34 |
| 2006/0265079 A1* | 11/2006 | D'Alessio, II | A61F 2/30721 623/20.15 |
| 2007/0276292 A1* | 11/2007 | Hansma | A61B 5/4504 600/587 |
| 2007/0299530 A1* | 12/2007 | Rhodes et al. | 623/20.32 |
| 2008/0306602 A1 | 12/2008 | Worland et al. | |
| 2011/0152724 A1 | 6/2011 | Hansma et al. | |
| 2011/0190898 A1* | 8/2011 | Lenz et al. | 623/20.32 |
| 2012/0006125 A1 | 1/2012 | Wen | |

* cited by examiner

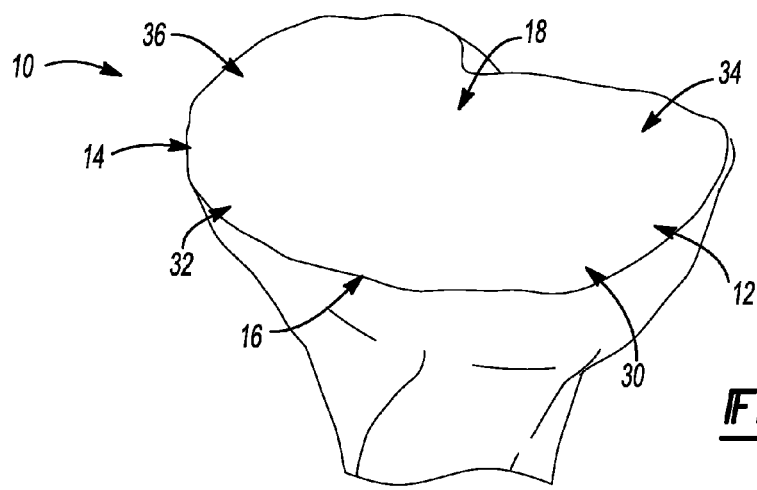
*Fig-1*
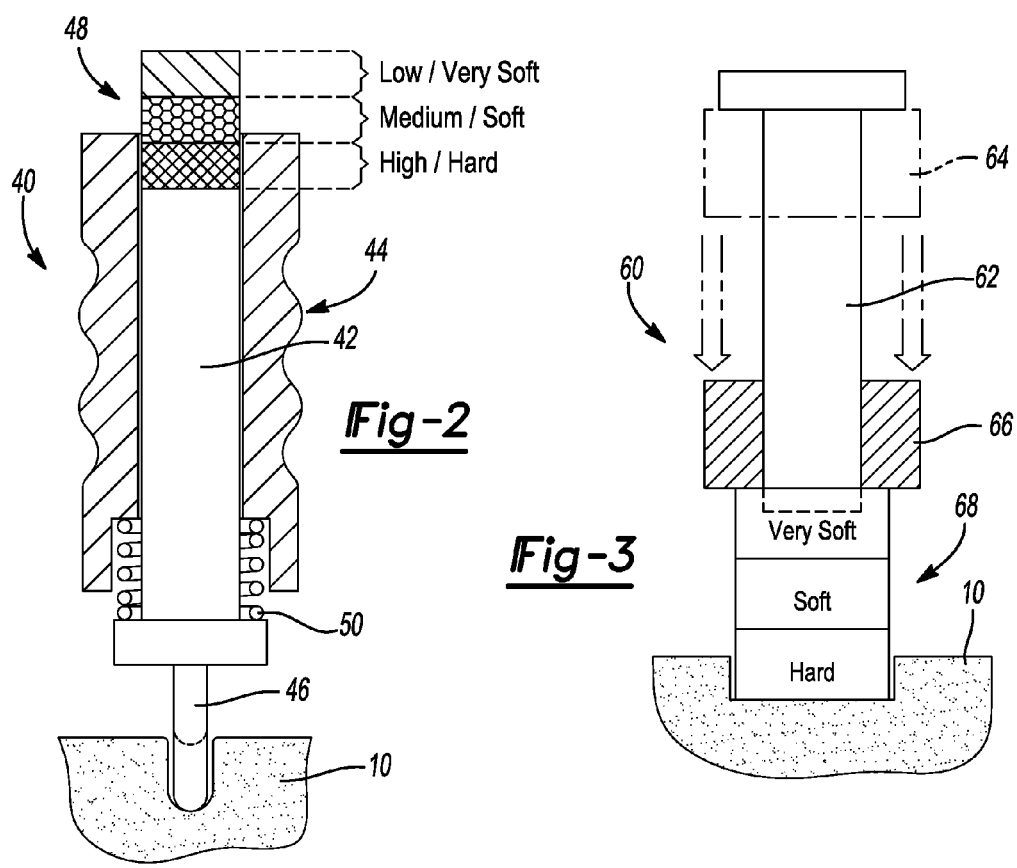
*Fig-2*
*Fig-3*

METHOD OF IMPLANTING A KNEE PROSTHESIS BASED ON BONE DENSITY

FIELD

The present disclosure relates to methods of implanting a tibial prosthesis onto a proximal tibia and more particularly, to a method of implanting a tibial component relative to a proximal tibia based on the bone density of the proximal tibia.

BACKGROUND

This section provides background information related to the present disclosure which is not necessarily prior art.

A knee joint prosthesis can generally comprise a femoral component and a tibial component. The femoral component and the tibial component can be designed to be surgically attached to the distal end of the femur and the proximal end of the tibia, respectively. In some instances, some portions of the proximal tibia may have different bone density than other portions of the proximal tibia. For example, the medial side tibial bone may be harder in density than the lateral side tibial bone. In this regard, it may be desirable to prepare specific areas of a tibia differently based on the bone density for receiving corresponding fixation structure configured on a tibial component.

SUMMARY

This section provides a general summary of the disclosure, and is not a comprehensive disclosure of its full scope or all of its features.

A method of implanting a prosthesis based on bone density of a bone is provided. A first bone density of the bone may be determined at a first portion of the bone. A second bone density of the bone may be determined at a second portion of the bone. A first desired amount of bone removal may be determined at the first portion of the bone based on the first bone density. A second desired amount of bone removal may be determined at the second portion of the bone based on the second bone density. The desired amounts of bone may be removed from the first and second portions of the bone. A prostheses may be selected and then be implanted onto the bone.

According to additional features, the first bone density may be determined by measuring the first bone density with a bone density gauge. The second bone density may be determined by measuring the second bone density with a bone density gauge. The first desired amount of bone removal may be determined by removing a first amount of bone based on a first bone density and a third amount of bone based on a third bone density. The first amount of bone may be different than the third amount of bone. The first bone density may be different than the third bone density. In other features, the second desired amount of bone removal may be determined by removing a second amount of bone based on a second bone density and a fourth amount of bone based on a fourth bone density. The second amount of bone may be greater than the fourth amount of bone. The second bone density may be greater than the fourth bone density. The bone may be a tibia. The prosthesis may be a tibial component.

The first portion of the tibia may be one of a medial side and a lateral side. The second portion of the tibia may be the other of the medial and lateral side. The first portion of the tibia may be one of an anterior side and a posterior side. The second portion of the tibia may be the other of the anterior side and the posterior side. According to some examples, removing the desired amount of bone may comprise reaming bone having a predetermined bone density.

Implanting the tibial component may comprise advancing the tibial component onto the proximal tibia wherein a medial and lateral portion of the tibial component advances with substantially equivalent resistance from the tibia.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a superior view of a proximal right tibia shown with areas of potential bone density measurement;

FIG. 2 is a cross-sectional view of a bone density gauge constructed in accordance to one example of the present disclosure;

FIG. 3 is a cross-sectional view of a second bone density gauge constructed in accordance with additional features of the present disclosure;

Corresponding reference numerals indicate corresponding parts throughout the several views of the drawings.

DETAILED DESCRIPTION

Figure 4:
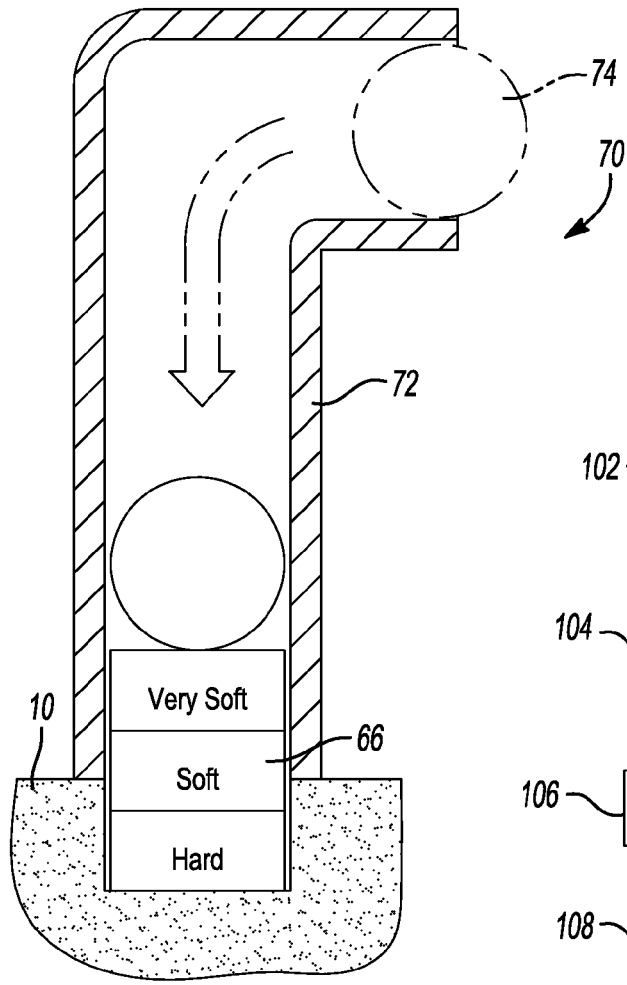
FIG. 4 is a bone density gauge constructed in accordance to yet another example of the present disclosure.

Example embodiments will now be described more fully with reference to the accompanying drawings.

The following discussion relates to a method of implanting a knee prosthesis based on bone density. The specific example used herein is directed toward a tibia, however it will be appreciated that the teachings may be equally applicable to a femur. Moreover, the following techniques may be used when implanting prostheses to other bones associated with other joints such as, but not limited to those associated with a hip, shoulder and elbow joint.

With initial reference to FIG. 1, a proximal tibia 10 is shown. In the example provided, the proximal tibia 10 is a right tibia that may be further defined by a medial side 12 and a lateral side 14. The proximal tibia 10 may be further defined by an anterior side 16 and a posterior side 18. It will be appreciated that while the proximal tibia 10 is shown and described herein with reference to a right tibia, the same methods may be applied to a left tibia. As will become appreciated from the following discussion, the present disclosure provides a method for implanting a tibial component, such as a tibial component selected from a kit of tibial components 20 shown in FIG. 6, based on the bone density of the proximal tibia 10.

In some examples, the bone density of the proximal tibia 10 may vary. Explained further, in some instances, the medial side 12 may have a bone density that is harder than a lateral side 14. Additionally, the bone density of the anterior side 16 and posterior side 18 may differ. In this regard, the present disclosure provides a method that more specifically prepares the proximal tibia 10 for receipt of a tibial component based on the bone density to account for any discrepancies. Explained further, in some instances, where the bone density is relatively soft, a surgeon may desire to provide more of a press-fit tibial component. In such an example, a tibial component may have a fixation structure (stem, keel, etc.) that is configured to create a press-fit with the tibial bone. In such a scenario, a surgeon may not necessarily want to specifically remove bone for receipt of the fixation structure and instead, rely more on the press-fit interaction of the fixation structure of the tibial component and the host tibia. Similarly, when the tibial bone has a relatively hard bone density, a surgeon may want to remove some of the bone for receipt of the fixation structure on the tibial component. In other examples, it may be desirable to remove a small portion of bone for bone densities having an intermediate hardness. In this regard, with more of the host bone removed at the higher density areas, the amount of press-fit required by a surgeon to accommodate the fixation structure may be reduced. In general, a surgeon will desire to achieve a relatively equivalent resistance across all portions (e.g., medial, lateral, anterior, posterior) of the tibial component during implantation onto the proximal tibia 10.

By way of example only, the proximal tibia 10 has been identified in FIG. 1 to include various potential locations for attaining a bone density measurement. Specifically, a first location 30 may include an anterior/medial location, a second location 32 may include an anterior/lateral location, a third location 34 may provide a posterior/medial location and a fourth location 36 may provide a posterior/lateral location. It will be appreciated that additional or fewer areas on the proximal tibia 10 may be used to determine bone density.

According to the present disclosure, the bone density may be determined in any manner. For example, some methods may determine bone density of the proximal tibia 10 using various imaging modalities such as, but not limited to a computed tomography (CT) scan or magnetic resonance imaging (MRI). In other examples, a bone density gauge may be used to measure the bone density. In still other examples, a combination of imaging and bone density gauge measurements may be obtained.

FIG. 2 illustrates a bone density tool or gauge 40 constructed in accordance to one example of the present disclosure. The bone density gauge 40 may generally include a shaft 42, a handle 44, a bone indenter 46, a density scale 48, and a compression spring 50. In general, the handle 44 may be translated toward the proximal tibia 10 which activates the compression spring 50 to load the bone indenter 46 with a known force. The harder the bone (higher bone density), the more the compression spring 50 compresses and the more the density scale 48 is exposed above the handle 44 to display an assessment of bone quality. The configuration of the bone density gauge 40 is merely exemplary.

As shown in FIG. 3, a second bone density tool or gauge 60 may include a shaft 62, a weight 64, and a bone indenter 66. The bone density gauge 60 may generally comprise a gravity based device that operates by dropping the weight 64 from a position generally on top of the shaft 62 such that the weight 64 drops onto the indenter 66. A scale 68 may be positioned between the proximal tibia 10 and the indenter 66. The level of penetration into the proximal tibia 10 determines the bone density. The configuration of the bone density gauge 60 is merely exemplary.

FIG. 4 illustrates another bone density tool or gauge 70 constructed in accordance to the present disclosure. The bone density gauge 70 may also be a gravity based gauge like the bone density gauge 60 described with respect to FIG. 3. The bone density gauge 70 generally includes a cannulated tube 72 and a ball 74. The ball 74 may be dropped down the cannulated tube 72 and onto a bone indenter 66. The level of penetration into the proximal tibia 10 determines the bone density. Again, it will be appreciated that the bone density gauges 40, 60 and 70 described above are merely exemplary and other bone density gauges may be employed for use with the method provided in the present disclosure.

Figure 5:
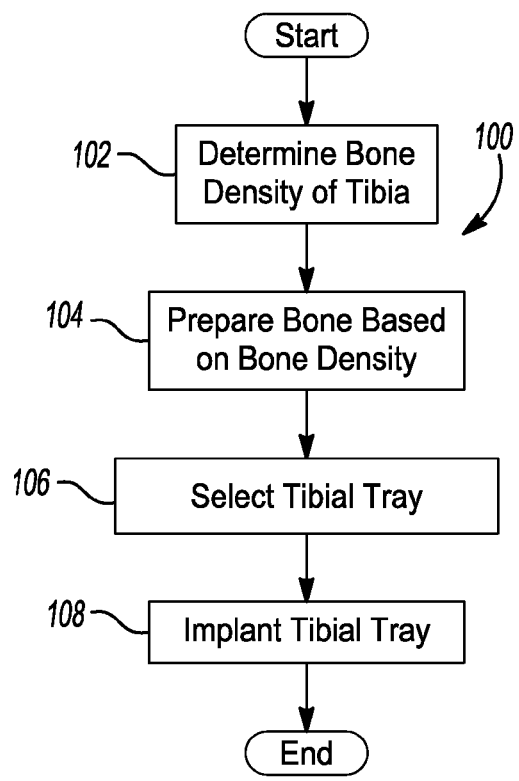
FIG. 5 is a flow diagram illustrating exemplary method steps of implanting a tibial tray based on bone density according to one example of the present disclosure.

Turning now to FIG. 5, an exemplary flow diagram 100 illustrating a method of implanting a tibial component based on the bone density of a proximal tibia 10 is shown. At 102, a surgeon may determine the bone density of the proximal tibia 10. Again, the bone density may be determined by any method such as a CT scan and/or a bone density gauge. The bone density may be determined at multiple areas of the proximal tibia 10 such as at the first, second, third and fourth locations 30, 32, 34 and 36 identified in FIG. 1 and discussed above.

Figure 6:
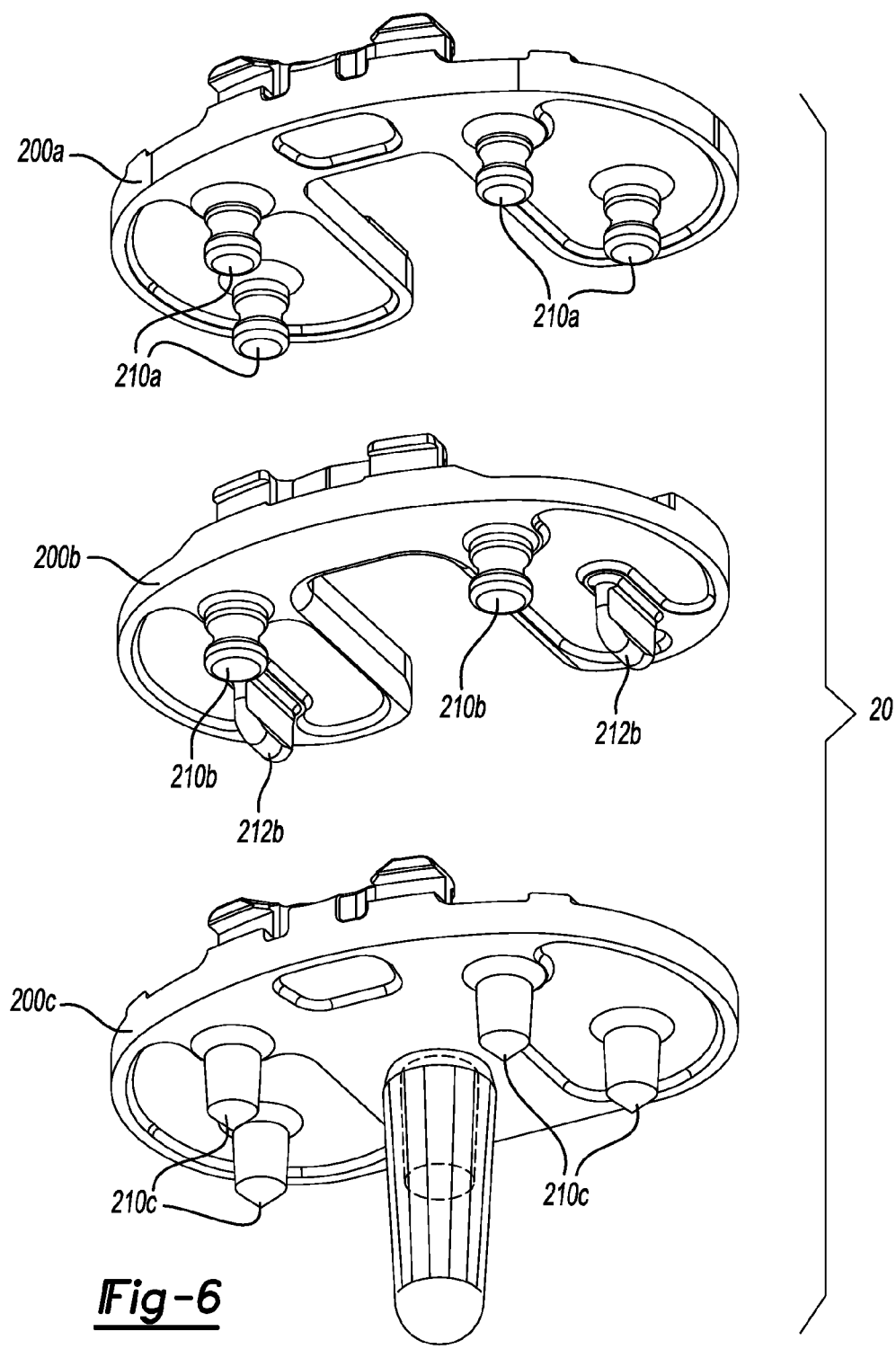
FIG. 6 is a kit having a plurality of tibial trays each having a bone engaging side comprising various fixation structures.

Once the bone density has been determined, the proximal tibia 10 may be prepared at 104 based on the bone density. As described above, it may be desirable to accommodate for more of a press-fit relationship between the tibial tray and the host tibia for a softer bone density area. Conversely, it may be desirable to drill and/or ream a higher density area of a proximal tibia to accommodate a fixation structure of a tibial tray during a press-fit. In this regard, the proximal tibia 10 may be prepared accordingly to accommodate similar press-fit forces across the entire proximal tibia 10 during advancement of the tibial component onto the proximal tibia 10. In 106, a tibial tray may be selected such as from the kit 20 (FIG. 6). In 108, the tibial component may be implanted.

With reference to FIG. 6, an exemplary kit of tibial components 20 is shown. The kit of tibial components 20 illustrated generally includes tibial components 200A, 200B, and 200C. The tibial components 200A, 200B, and 200C are merely exemplary. In this regard, other tibial tray configurations having other fixation structures may be provided. The tibial tray 200A may comprise tibial pegs 210A. The tibial tray 200B may comprise tibial pegs 210B. The tibial tray 200B may also incorporate tibial keels 212B. The tibial tray 200C may comprise pegs 210C. Other tibial tray configurations may be provided having other combinations of fixation structures within the scope of the present disclosure. Again, it will be appreciated that the surgeon may intraoperatively select a tray that may be particularly suited for interfacing with the measured bone density of the proximal tibia 10 of the particular patient.

Each of the tibial components 200A, 200B, and 200C may be patient-specific, semi-custom or off-the-shelf implants. A custom-made implant is a patient-specific, one-of-a-kind implant specifically made for a particular patient, and consequently there is no inventory associated with such an implant. Standard or off-the-shelf implants are available and stocked in a number of sizes, typically six or more, and a number of configurations or types, including bilateral or unilateral implants, constrained, semi-constrained, mobile, etc. Because of the variety of sizes and configurations that are kept in stock to be accommodated by different patients, a large inventory of standard implants is created, and several molds for each type and size of implant may be used. Semi-custom implants can provide an intermediate solution between custom-made and off-the-shelf implants. Semi-custom implants reduce the size of inventory and molds required for production, while allowing some degree of patient-specific customization. Additional description of patient-specific implants and semi-custom implants and their implementations may be found in co-pending patent application Ser. No. 12/103,824, filed Apr. 16, 2008 and entitled: Method And Apparatus For Manufacturing An Implant, the disclosure of which is hereby incorporated by reference.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a prosthesis having first and second fixation features based on bone density of a bone, the method comprising:
   determining a first bone density of the bone at a first portion of the bone;
   determining a second bone density of the bone at a second portion of the bone;
   determining a first desired amount of bone removal at the first portion of the bone based on the first bone density;
   determining a second desired amount of bone removal at the second portion of the bone based on the second bone density;
   removing the desired amounts of bone from the first and second portions of the bone; and
   implanting the prosthesis onto the bone by inserting the first fixation feature into the bone at the first portion of bone and the second fixation feature into the bone at the second portion of bone;
   wherein when the first bone density is greater than the second bone density, the first desired amount of bone removal is greater than the second desired amount of bone removal such that similar press fit forces are formed on each fixation feature at the first and second portions of the bone.

2. The method of claim 1 wherein determining a first bone density further comprises:
   measuring the first bone density with a bone density gauge having an indenter movable relative to a shaft or tube.

3. The method of claim 2 wherein determining a second bone density further comprises:
   measuring the second bone density with a bone density gauge.

4. The method of claim 1 wherein determining the first desired amount of bone removal further comprises:
   determining to remove one of a first amount of bone based on a first bone density and a third amount of bone based on a third bone density.

5. The method of claim 4 wherein the first amount of bone is different than the third amount of bone and the first bone density is different than the third bone density.

6. The method of claim 1 wherein determining the second desired amount of bone removal further comprises:
   determining to remove a second amount of bone based on a second bone density and fourth amount of bone based on a fourth bone density, wherein the second amount of bone is greater than the fourth amount of bone and the second bone density is greater than the fourth bone density.

7. The method of claim 1 wherein the bone is a tibia and wherein the first portion of the tibia is one of a medial side and a lateral side and the second portion is the other of the medial side and the lateral side.

8. The method of claim 1 wherein the bone is a tibia and wherein the first portion of the tibia is one of an anterior side and a posterior side and the second portion is the other of the anterior side and the posterior side.

9. The method of claim 1 wherein removing the first desired amount of bone comprises removing high quality bone above a predetermined density value.

10. The method of claim 9 wherein the bone is a tibia and wherein implanting the prosthesis comprises advancing a tibial component onto the proximal tibia wherein a medial and lateral portion of the tibial component advances with substantially equivalent resistance from the tibia.

11. A method of implanting a prosthesis based on bone density of a bone, the method comprising:
   intraoperatively measuring a first bone density of a prepared surface of the bone at a first portion of the bone using a bone density gauge;
   intraoperatively measuring a second bone density of the prepared surface of the bone at a second portion of the bone using the bone density gauge;
   determining to remove a portion of bone at one of the first and second portions of bone based on a measured bone density above a predetermined value;
   removing the portion of bone having a measured bone density above the predetermined value to form a fixation feature socket;
   selecting a prostheses having first and second fixation features; and
   implanting the prosthesis onto the bone by inserting one of the first and second fixation features into the fixation socket and the other of the first and second fixation features into a surface of the bone not having bone removed.

12. The method of claim 11 wherein measuring the first bone density further comprises:
   measuring the first bone density with the bone density gauge, wherein the bone density gauge provides a visual indication of the bone density by positioning an indenter of the bone density gauge relative to a scale on the bone density gauge.

13. The method of claim 12 wherein measuring the second bone density further comprises:
   measuring the second bone density with the bone density gauge.

14. The method of claim 11 wherein the bone is a tibia and the first portion of the bone is one of a medial side and a lateral side and the second portion is the other of the medial side and the lateral side.

15. The method of claim 11 wherein the bone is a tibia and wherein the first portion of the tibia is one of an anterior side and a posterior side and the second portion is the other of the anterior side and the posterior side.

16. The method of claim 11 wherein removing the portion of bone comprises reaming bone having a predetermined bone density.

17. The method of claim 16 wherein the bone is a tibia and wherein implanting the prosthesis comprises advancing a tibial component onto the proximal tibia wherein one of a medial portion and a lateral portion of the tibial component advances with substantially equivalent resistance from the tibia into each of the reamed bone and un-reamed bone.

18. The method of claim 11 wherein implanting the prosthesis into the bone comprises advancing the first and second fixation features into the bone to experience similar press-fit forces for the first and second fixation features at the first and second portions of the bone.

19. A method for implanting a prosthesis having first and second fixation features of the same size and disposed in a predetermined fixed relational arrangement based on bone density of a bone, the method comprising:
   determining a first bone density of the bone at a first portion of the bone located to receive the first fixation feature;
   determining a second bone density of the bone at a second portion of the bone located to receive the second fixation feature, wherein the second bone density of the bone is different than the first bone density of the bone;
   removing different amounts of bone from the first and second portions of the bone to form first and second holes of different sizes in order to achieve similar press-fit forces for the first and second fixation features at the first and second portions of the bone, respectively; and
   inserting the first and second fixation features into the first and second portions of the bone.

* * * * *